United States Patent [19]
Webb et al.

[11] Patent Number: 5,576,617
[45] Date of Patent: *Nov. 19, 1996

[54] APPARATUS & METHOD FOR MEASURING THE AVERAGE ASPECT RATIO OF NON-SPHERICAL PARTICLES IN A SUSPENSION

[75] Inventors: Terence W. Webb; Leonard F. Gate, both of St. Austell, United Kingdom

[73] Assignee: ECC International Limited, Great Britain

[*] Notice: The term of this patent shall not extend beyond the expiration date of Pat. No. 5,128,606.

[21] Appl. No.: 302,851

[22] PCT Filed: Jan. 17, 1994

[86] PCT No.: PCT/GB94/00090

§ 371 Date: Sep. 16, 1994

§ 102(e) Date: Sep. 16, 1994

[87] PCT Pub. No.: WO94/16308

PCT Pub. Date: Jul. 21, 1994

[30] Foreign Application Priority Data

Jan. 18, 1993 [GB] United Kingdom ............... 9300845

[51] Int. Cl.[6] ............... G01N 15/02; G01N 27/00
[52] U.S. Cl. ............... 324/71.4; 324/439; 137/5; 73/61.41; 73/61.08
[58] Field of Search ............... 324/71.1, 71.4, 324/439, 446, 448–450, 699, 716; 73/61.41, 861.08; 137/5

[56] References Cited

U.S. PATENT DOCUMENTS

| 4,027,162 | 5/1977 | Knollenberg | 250/345 |
|---|---|---|---|
| 4,420,720 | 12/1983 | Newton et al. | 324/71.4 |
| 4,434,398 | 2/1984 | Berg et al. | 324/71.4 |
| 4,525,666 | 6/1985 | Groves | 324/71.4 |
| 4,778,657 | 10/1988 | Spohr | 324/71.4 |
| 4,906,936 | 3/1990 | Butas | 324/7.14 X |
| 5,128,606 | 7/1992 | Gate et al. | 324/439 X |

FOREIGN PATENT DOCUMENTS

| 2240398 | 7/1991 | United Kingdom . |
|---|---|---|
| WO88/05532 | 7/1988 | WIPO . |

*Primary Examiner*—Kenneth A. Wieder
*Assistant Examiner*—Diep Do
*Attorney, Agent, or Firm*—Klauber & Jackson

[57] ABSTRACT

Method and apparatus for obtaining the average aspect ratio of non-spherical particles in suspension. The particles are caused to orient generally in one direction and the conductivity of the particles are measured in such direction while simultaneously measuring the conductivity of the particles in a traverse direction. The difference between the two conductivity measurements is indicative of the average aspect ratio of the particles in suspension.

14 Claims, 4 Drawing Sheets

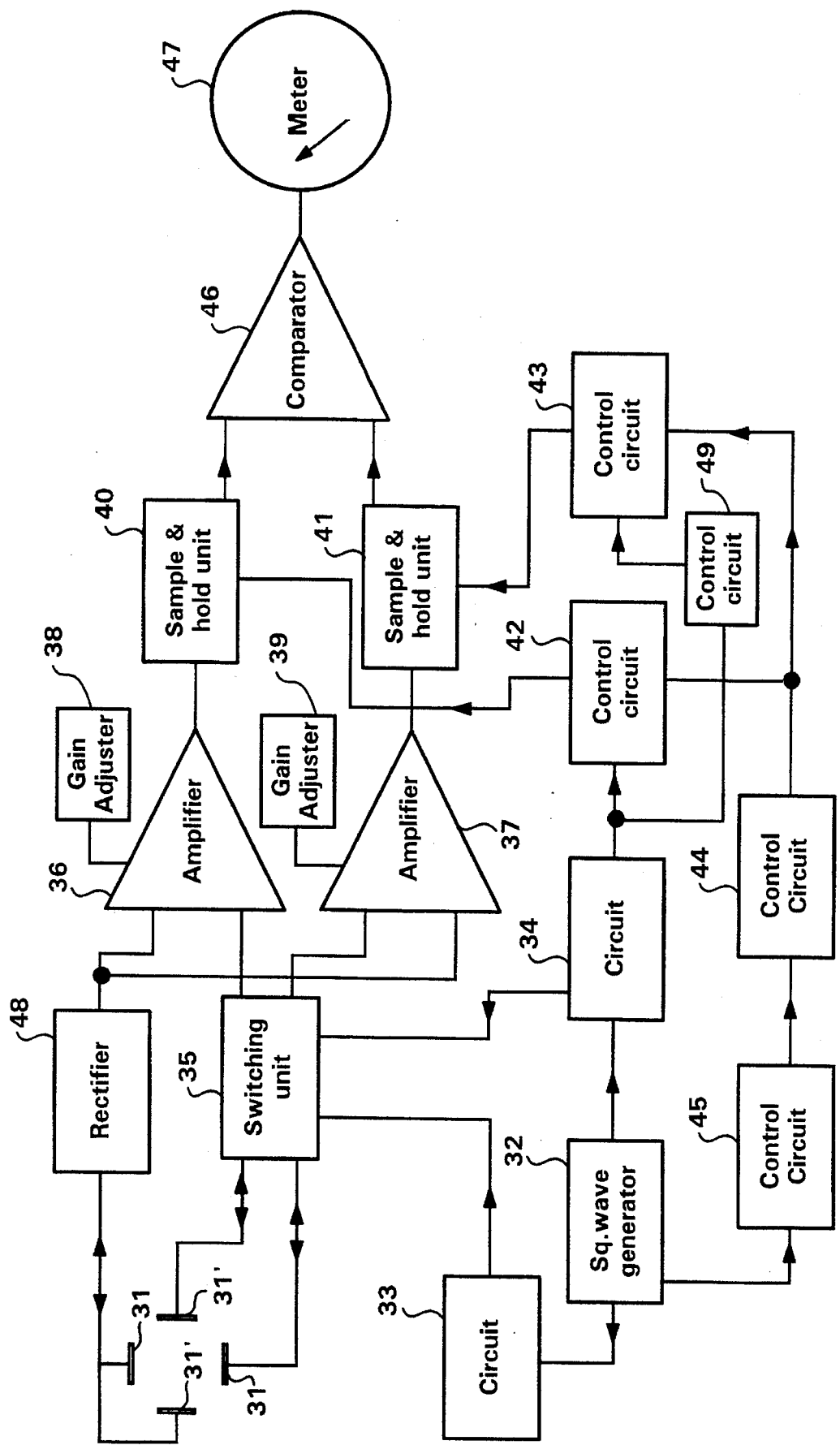

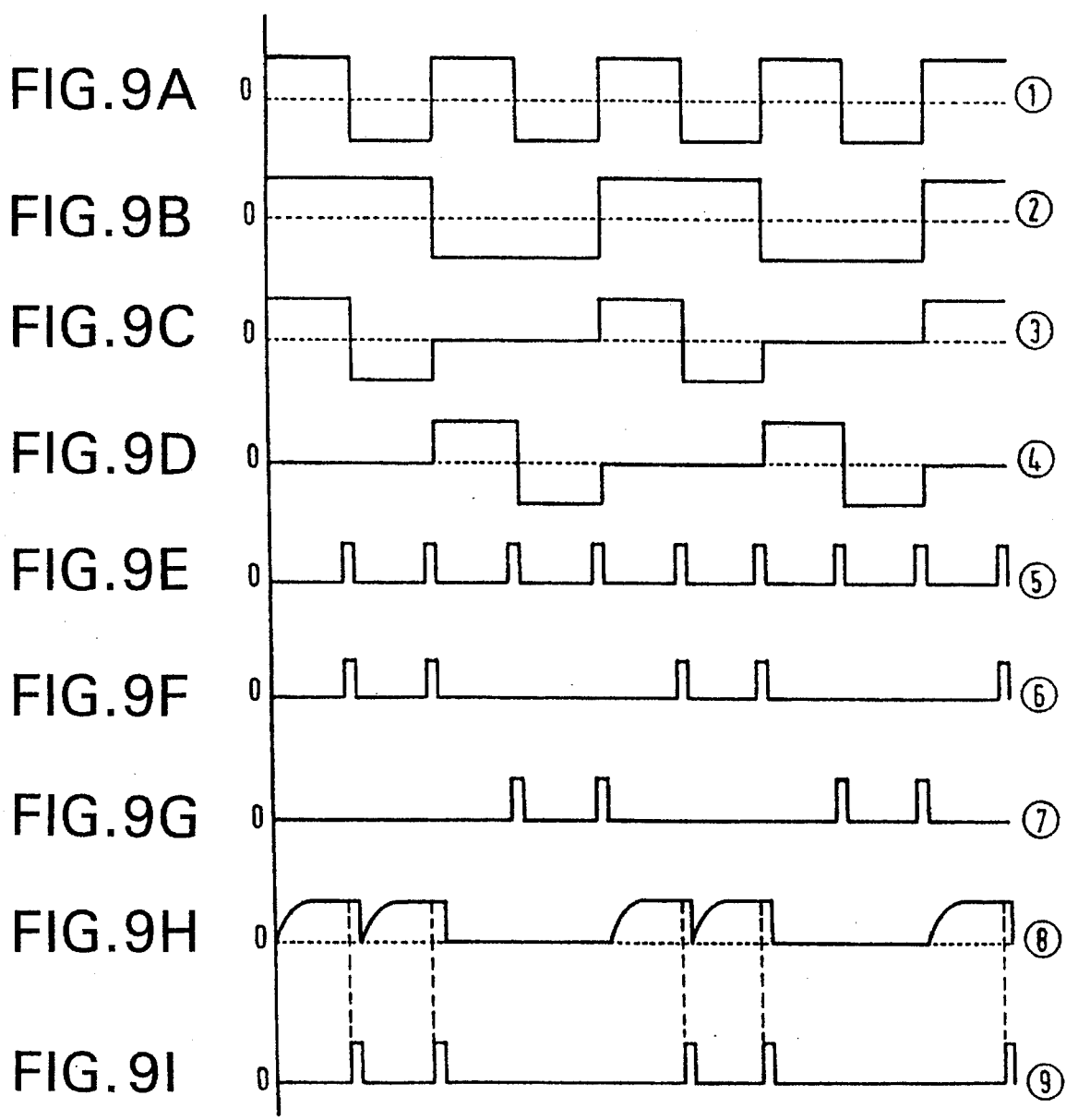

APPARATUS & METHOD FOR MEASURING THE AVERAGE ASPECT RATIO OF NON-SPHERICAL PARTICLES IN A SUSPENSION

The invention relates to apparatus and a method for measuring the average aspect ratio of non-spherical, e.g. laminar or ellipsoidal, particles in a suspension. In particular, although not exclusively, the invention relates to the measurement of the average aspect ratio of kaolin particles in suspension in a fluid.

In many applications of particulate solid materials the aspect ratio of the particles of the material is a parameter which profoundly affects the performance of the material. For example, if the particulate material is used in a composition for coating paper, the surface finish of the paper is determined to a large degree by the average aspect ratio of the particles. If it is required to produce a coated paper which has a smooth, glossy finish the particulate material will need to have a different average aspect ratio from that required if the coated paper is to have a matt surface with greater ink absorbency.

FIG. 1 illustrates the meaning of the expression "aspect ratio" used in this application. The expression "aspect ratio" means "the diameter of the circle of area equivalent to that of a face of the particle divided by the mean thickness of that particle". In FIG. 1 a kaolin particle P is shown with a superimposed circle having an area equivalent to that of the face of the particle. The diameter of that circle is d, the thickness of the particle is t and the aspect ratio of the particle is d/t.

It has previously been found that the average aspect ratio of particles in a suspension may be calculated from the measurement of the conductivity of the suspension. In the present applicant's previous British Patent Application No. 9101291.4 (Publication No. 2240398) a method and an apparatus are described for obtaining a measurement indicative of the aspect ratio of non-spherical particles in suspension. The conductivity of the suspension is measured between points for two different orientations of the particles in suspension and the difference between the two measured conductivities is used as an indication of the particle aspect ratio. The particle orientation may be aligned for the first conductivity measurement and may be aligned transverse to the first orientation direction, or have random alignment, for the second conductivity measurement. The specification also discloses a further alternative in which there is a single aligned orientation but transversely directed conductivity measurements.

However, problems have been discovered with this prior art apparatus and method, in particular with the obtaining of consistent correlation of aspect ratio measurement with change of conductivity. It has been determined that variations in temperature of the particle suspension can result in significantly erroneous readings for the comparative conductivity measurements. In particular this may occur in the case where measurement is effected after a flow of suspension is stopped to allow the asymmetric particles to revert to a random orientation through the action of Brownian forces. This may take several minutes for large colloidal particles and during this period the static suspension may undergo a small temperature change as it comes into equilibrium with its surroundings. However, the electrical conductivity of solutions may vary significantly with temperature. This variation may typically be as much as 2% per °C. and, in the case of kaolinite suspensions, a temperature coefficient of 0.77% per °C. has been measured. As a result a relatively small change in temperature occurring over several minutes can lead to errors in the value for the conductivity and thus lead to errors in the shape factor computed from it.

To overcome this problem, control of the ambient temperature surrounding the conductivity cell or direct control of the suspension temperature has been considered. However to achieve this results in an increase in the complexity of the apparatus so increasing its size and cost. In addition, such an approach does not lend itself to continuous control in a production environment, e.g. where the aspect ratio measurement is used to control the mixing of particles from different sources or to control particle grinding equipment to achieve the desired average aspect ratio mix of the suspension.

The invention seeks to provide an improved apparatus and a method for obtaining a measure of the average aspect ratio of non-spherical particles in a suspension.

According to one aspect of the present invention there is provided a method of obtaining a measure of the average aspect ratio of non-spherical particles comprising the steps of:

obtaining a fully-deflocculated suspension of the particles;

causing the particles in the suspension to orientate generally in one direction;

measuring the conductivity of the particles suspension substantially in said one direction simultaneously or substantially simultaneously measuring the conductivity of the particle suspension in a direction transverse to said one direction; and using the difference in the two conductivity measurements as a measure of the average aspect ratio of the particles in suspension.

By measuring conductivity substantially simultaneously is meant sufficiently close in time before or after the other conductivity measurement that the temperature of the suspension being measured will be effectively the same for each measurement.

In the preferred method the particles are caused to orientate generally using a shear field by flowing the suspension through a conduit whereby the particles orientate such that their long axes are parallel to the direction of flow, which constitutes said one direction.

Preferably the conductivity measuring steps are alternated and repeated relatively rapidly and the results averaged. Preferably also each conductivity measurement is taken using an AC current so that polarisation effects are cancelled and therefore do not distort the results.

In an advantageous method the conductivity measurements are effected by using alternate full cycles of an AC square wave source for the alternate conductivity measurements.

According to a second aspect of the invention there is provided apparatus for obtaining a measure of the average aspect ratio of non-spherical particles, comprising:

a containment vessel for a fully-deflocculated suspension of the particles;

means for causing the particles in the suspension to orientate generally in one direction;

a first pair of electrodes for use in measuring the conductivity of the particle suspension in a direction aligned with said one direction;

a second pair of electrodes for use in simultaneously or substantially simultaneously measuring the conductivity of the particle suspension in a direction transverse to said one direction; and comparison means for comparing the conductivity measurements made using the first and second pairs of electrodes and for producing an output signal which is a measure of the average aspect ratio of the particles in suspension.

One electrode may be common to both pairs of electrodes. Additionally more than one conductivity measurement may be made for each direction, to enable measurements of conductivity aligned in direction but of opposite electrical sense so as to counteract external effects.

The electrodes may be in a single containment vessel or alternatively at least two vessels may be provided in each of which the particles in the suspension are given the same orientation, and in at least one of which the conductivity between two points in the suspension is measured in said one direction, and in at least one other of which the conductivity is measured in said transverse direction.

Conveniently the apparatus comprises a tubular containment vessel in which measurement of conductivity in the first direction is made between a first electrode which is mounted at or near the longitudinal axis of the vessel and a second, annular electrode which is mounted in the vessel surrounding and substantially coaxial with the first electrode, and in which the measurement of conductivity in the second direction is made between at least one pair of electrodes which are spaced apart longitudinally in the vessel.

Alternatively the apparatus may comprise a first tubular vessel having a wall of electrically conducting material in which the measurement of conductivity in the first direction is made between an electrode mounted at or near the longitudinal axis of the vessel and the electrically conducting wall of the chamber, and a second tubular vessel in which the measurement of conductivity in the second direction is made between at least one pair of electrodes which are spaced apart longitudinally in the vessel.

The tubular vessel or vessels may form part of a conduit in a production facility, whereby the measurement of particle shape can be used in a control loop system to achieve a desired average aspect ratio by controlling admixture of particles from different sources or by control of particle grinding means.

The electrodes are preferably of a non-corrosive material such as carbon or stainless steel.

For a better understanding of the present invention, and to show how it may be brought into effect, reference will now be made, by way of example, to the following drawings in which:

FIG. 8 shows a block diagram of a measurement circuit for use with the apparatus in accordance with the invention; and FIG. 9 shows the wave forms present at selected points in the circuit of FIG. 8.

The apparatus of the invention may be used to obtain a measure of the average aspect ratio of particles in a suspension in accordance with a theoretical treatment given by H. Fricke in an article entitled, "A Mathematical Treatment of the Electric Conductivity and Capacity of Disperse Systems", (Phys. Rev.,24, 1924, pp 575–587) which discusses the conductivity of randomly orientated ellipsoidal particles in a suspension.

Figure 2:
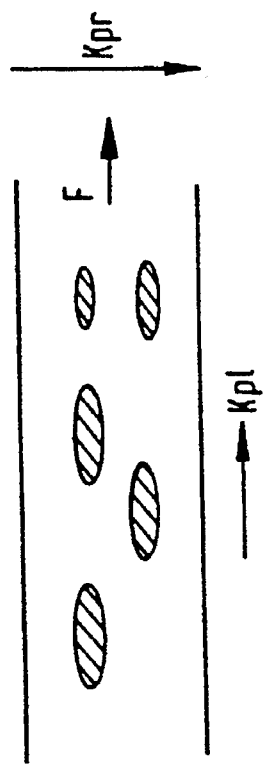
FIG. 2 is a diagrammatic representation of a suspension of ellipsoidal particles flowing along a conduit.

According to Fricke, if ellipsoidal particles are orientated in a shear gradient, for example, with their major axial dimension aligned as shown in FIG. 2 and the conductivity is measured in a direction parallel ($K_{pl}$) and perpendicular ($K_{pr}$) to the particle major axial dimension, then the relationship between the directional conductivity and the shape factor of the particles is given by the following equations:

$$\frac{K_{pl}}{K_{pr}} = \frac{1 + 2\left(\frac{K_2}{K_1}\right)\left(\frac{R}{1-R}\right)B}{1 + 2\left(\frac{R}{1-R}\right)B} \cdot \frac{1 + \left(\frac{R}{1-R}\right)C}{1 + \left(\frac{K_2}{K_1}\right)\left(\frac{R}{1-R}\right)C} \quad (1)$$

where R=volume fraction occupied by the particles in suspension;

$K_2$=particle conductivity;
$K_1$=fluid phase conductivity;

$$B = \frac{1}{2 + M(K_2/K_1 - 1)}$$

$$C = \frac{1}{1 + (1-M)(K_2/K_1 - 1)}$$

The term M which occurs in B and C contains the information concerning particle shape and is given, for oblate spheroids, by:

M=($\phi$−sin2$\phi$/2)/sin$^3$$\phi$ where cos$\phi$=a/b with
2a=minor axis (thickness) of particles
2b=2c=major axis (diameter) of particles.

If a value for the term $K_2/K_1$ is known, or can be assumed, then equation 1 enables the measured quantity $K_{pl}/K_{pr}$ to be related to the aspect ratio (a/b) of the particles.

Equation (1) indicates that the measured quantity $K_{pl}/K_{pr}$ is independent of the particle size (i.e. on the major axis diameter 2b), but depends only on the ratio (a/b). If this ratio varies within the material in suspension, then only a single mean value will be obtained by the method described above. This single mean value will be based on the relative volumes occupied by the various component particles, because equation 1 indicates that it is only the parameter R which controls the value of $K_{pl}/K_{pr}$.

Figure 3:
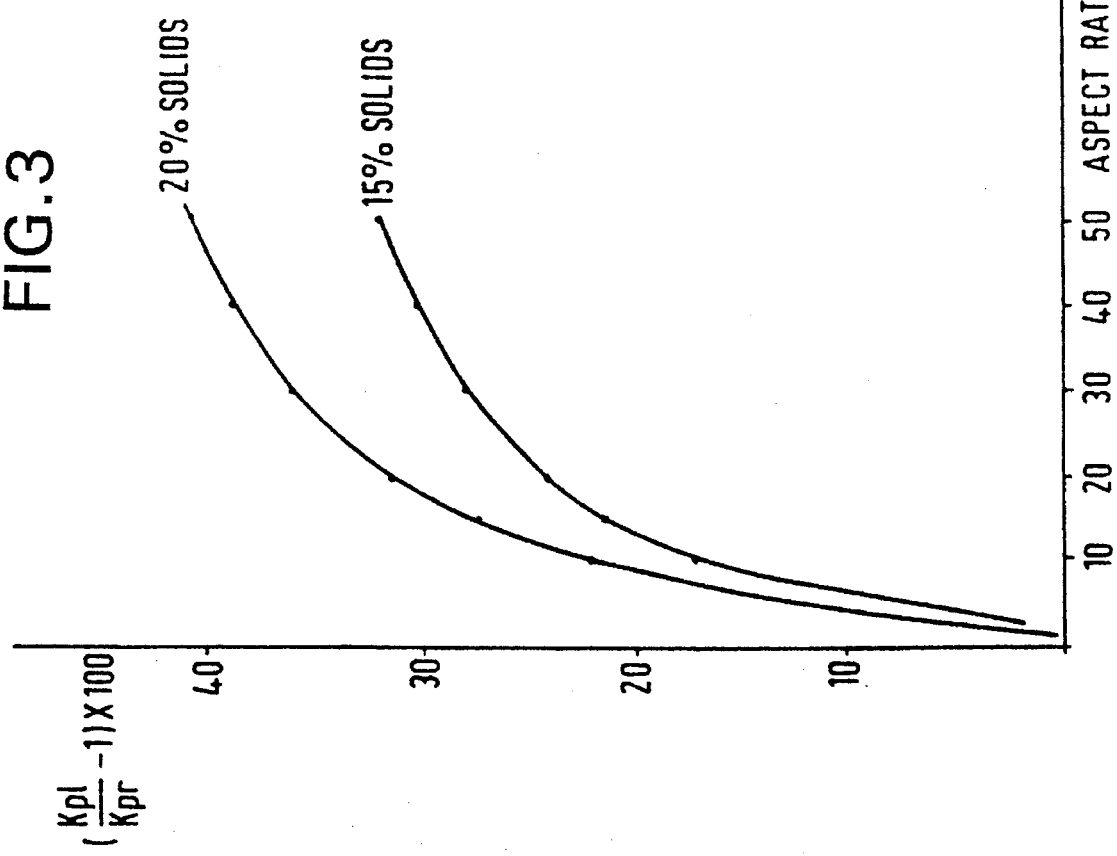
FIG. 3 is a graph showing the relationship between the difference between two conductivity measurements, each taken between two points in the suspension but in mutually perpendicular directions, and the aspect ratio.
Figure 1:
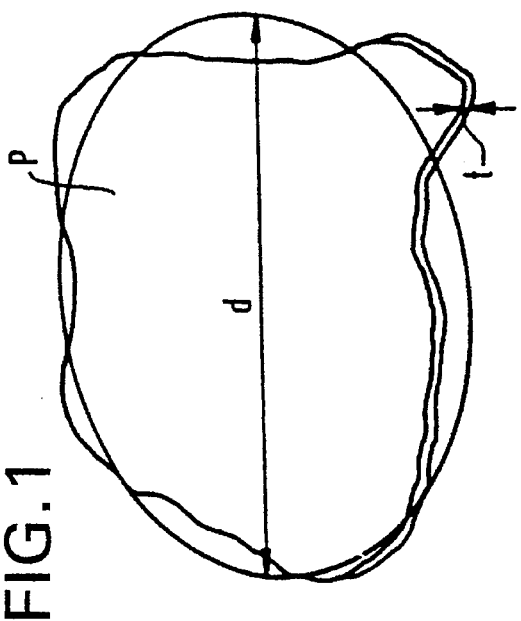
FIG. 1 shows a platelet-like particle.

In order to illustrate the use of equation 1 it is possible to calculate how the value ($K_{pl}/K_{pr}$−1).100 changes with aspect ratio values at a given solids concentration in the suspension as shown in FIG. 3. For this purpose, a value for the parameter $K_2/K_1$ of 0.12 has been assumed, based on practical experience with the method. It can be seen that, as the aspect ratio of a particle increases in value, then the change in conductivity values measured in different directions through a suspension of the orientated particles also increases, enabling a value for the aspect ratio to be estimated. Two different values for the suspension solids concentrations have been included in these calculated examples, namely 15% by weight and 20% by weight, respectively, of solids.

Figure 4:
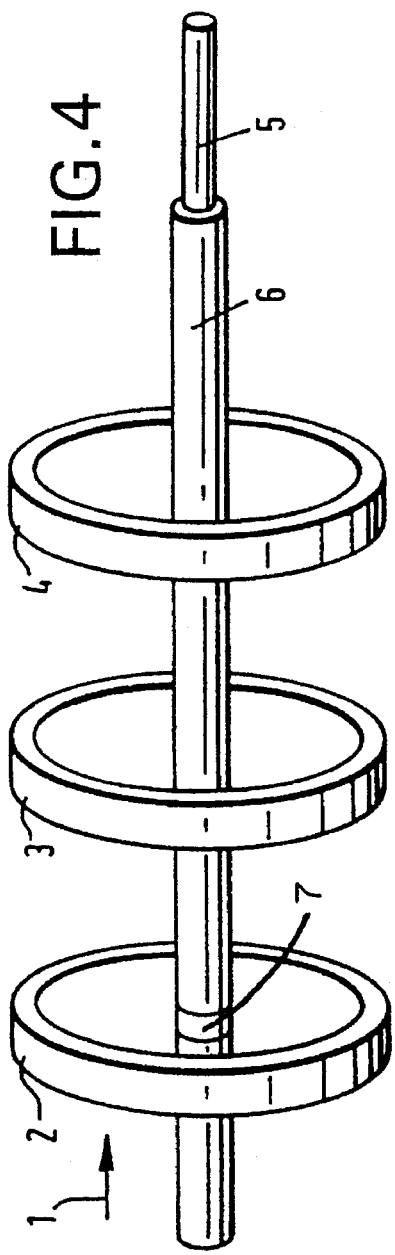
FIG. 4 shows the arrangement of electrodes in a first embodiment of the apparatus of the invention.

FIG. 4 shows diagrammatically an arrangement of electrodes which may be used to make conductivity measurements so as to obtain a measure of the average aspect ratio of particles in an aqueous suspension in accordance with the mathematical treatment given above.

The apparatus for measuring the conductivity of the solution includes a tubular measuring vessel (not shown) which contains the aqueous suspension.

Three annular carbon electrodes 2, 3 and 4 are set in the cylindrical wall of the measuring vessel. A stainless steel rod 5, covered within the measuring vessel, substantially completely by a nylon sleeve 6 is fixed along the longitudinal axis of the measuring chamber. At the centre of the annular electrode 2 a gap is left in the sleeve 6, which gap is filled by a carbon collar fitting tightly on the stainless steel rod 5, the carbon collar forming a fourth electrode 7.

Figure 5:
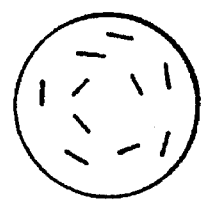
FIG. 5 is a diagrammatic representation of a cross section of the conduit shown in FIG. 2 showing radial symmetry of orientation of the particles.

An aqueous suspension of non-spherical particles flows in the direction of the arrow 1 through the measuring vessel. In this case the velocity gradient in the flowing suspension increases linearly with radial distance from the longitudinal axis of the measuring chamber causing the particles to align parallel to the axis according to well known behaviour. When the particles have a shape which approximates to that of oblate spheroids, the major axial dimension will be parallel to the longitudinal axis and, on average, perpendicular to the radial direction. The orientation of particles under these shear field conditions is represented diagrammatically in FIG. 5 which shows a transverse cross section through the measuring vessel. Thus, measurements of conductivity made in the stream of flowing suspension between the axial electrode 7 and the annular electrode 2 give the conductivity in a direction perpendicular to the major axial dimension of the particles ($K_{pr}$), and between the central annular electrode 3 and the two outer annular electrodes 2 and 4 connected together to give the conductivity in the direction generally parallel to the flow direction and to the major axial dimension of the particles ($K_{pl}$).

If the case of a suspension flowing through a tubular measuring chamber is compared with the case of random orientation of the particles, as obtains, for example, in a non-flowing suspension, the conductivity $K_{pr}$ is higher in the flowing state and the conductivity $K_{pl}$ is lower, than in the non-flowing state.

Figure 6:
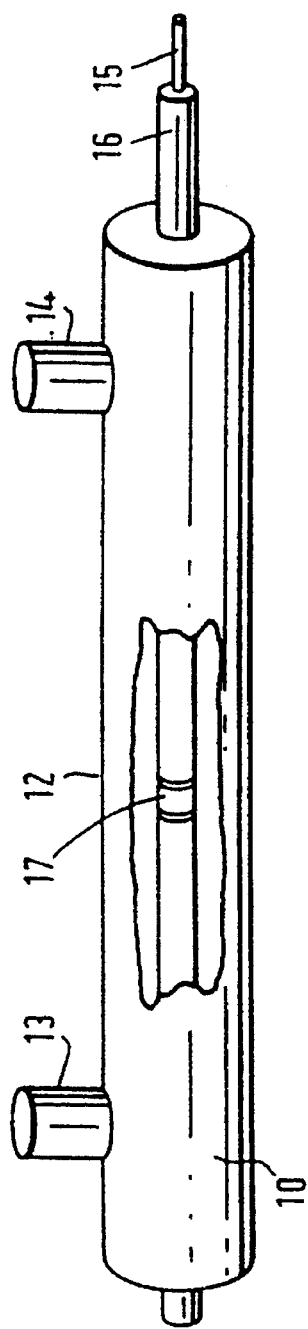
FIG. 6 shows a first tubular vessel.
Figure 7:
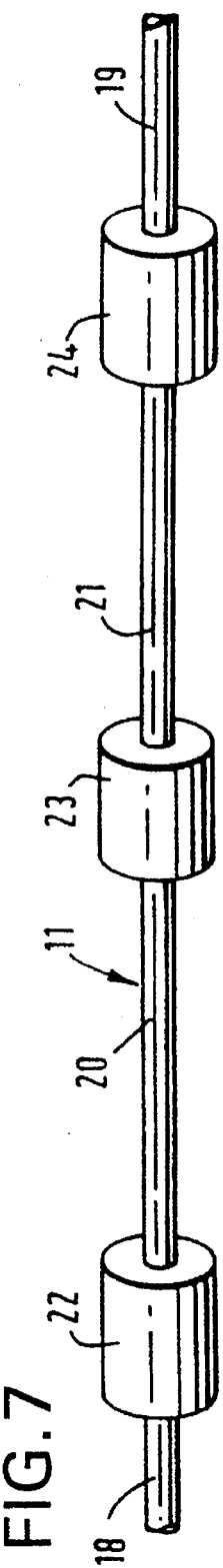
FIG. 7 shows an electrode arrangement for a second tubular vessel, in a second embodiment of the apparatus of the invention.

FIGS. 6 and 7 show a further embodiment of the apparatus of the invention. An aqueous suspension of non-spherical particles is caused to flow at a substantially uniform velocity through a first measuring vessel 10 (FIG. 6) and then through a second measuring vessel 11 (FIG. 7).

Measuring vessel 10 comprises a cylindrical shell 12 of stainless steel provided with an inlet 13 and an outlet 14 for the flowing suspension. A stainless steel rod 15 is fixed along the longitudinal axis of the vessel and is covered within the measuring vessel 10 substantially completely with a nylon sleeve 16. At the mid point of the measuring vessel a gap is left in the sleeve 16, which gap is filled with a carbon collar fitting tightly on the stainless steel rod 15, which forms an electrode 17.

The second measuring vessel 11 comprises a nylon inlet tube 18 and a nylon outlet tube 19 and two further equal lengths of nylon tubing 20 and 21. The lengths of tubing are joined together by three cylindrical carbon electrodes 22, 23 and 24, each of which has an axial bore into which the nylon tubing fits tightly. Tubes 18 and 20 each fit into the bore of electrode 22 with a gap left between the two ends of the tubes within the bore. Tubes 20 and 21 each fit in a similar manner into the bore of electrode 23, and tubes 21 and 19 into the bore of electrode 24.

The conductivity in the direction perpendicular to the major axial dimension of the particles ($K_{pr}$) is measured between the axial electrode 17 and the stainless steel shell 12. The conductivity in the direction parallel to the major axial dimension of the particles ($K_{pl}$) is measured between the central electrode 23 and the two outer electrodes 22 and 24 connected together. The two conductivity measurements are then used as indicated above to provide a measure of the average aspect ratio of the particles in the suspension.

A complete measuring circuit for the measurement in accordance with this invention will now be described with reference to FIGS. 8 and 9.

Two pairs of conductivity-measurement electrodes 31 and 31' corresponding to the electrodes described above are mounted in a measuring vessel (not shown) containing a flowing particle suspension. The electrodes are arranged so that one pair of electrodes measures the conductivity of the particle suspension in the vessel in a direction parallel to the aligned major axes of the particles and the other pair of electrodes measures the conductivity of the solution in a direction perpendicular to the major axes of the particles. As illustrated in FIG. 4 one electrode 31,31') is common to both the transverse and the lateral measurement pair of electrodes.

A square wave generator 32 is provided which generates a 70 hertz square wave. This signal, shown at waveform 1 in FIG. 9, is fed to a constant current regulation circuit 33 and to a divide by two unit 34. Signals from the current regulation circuit 33 and the divide by two circuit 34 are fed to the switching unit 35, from which alternate full cycles are fed to each pair of electrodes in turn. As a result measurements of the conductivity in the directions perpendicular and parallel to the particle orientation are taken at $\frac{1}{70}$ second intervals.

The signals resulting from the constant amplitude current fed to the lateral and transverse electrode pairs are illustrated as waveforms 3 and 4 respectively in FIG. 9. The signals are rectified by rectifier 48 and then fed to amplifiers 36 and 37. In operation, the amplifiers 36 and 37 have their gains set by means of gain adjusters 38 and 39 to give an output value in the region of 50% of output swing and exactly equal to each other when a totally homogenous or particle free sample, of similar conductivity to the kaolin slurry to be monitored, is placed in the measuring vessel.

The output of the amplifiers 36 and 37 is fed to sample and hold units 40 and 41 respectively. The control circuitry for the sample and hold units comprises circuits 42, 43, 44, 45 and 49. Circuits 42 and 43 are two-input AND circuits, 49 is an inverter, 45 is a pulse generator and 44 is a delay circuit.

In order for the measurement of the signal from the electrodes to be as accurate as possible, the output from the amplifiers 36 and 37 is sampled by the sample and hold units 40 and 41 about 80% of the way through a half-cycle. This is done because the rise of the voltage signal from the electrodes in response to the pulses 3 or 4 (FIG. 9) is delayed because of capacitive effects. Thus in order to achieve accurate measurements the control circuits 42, 43, 44 and 45 and 49 operate so as to cause the sampling of the output of the amplifiers 36 and 37 at a point 80% through each half cycle.

Pulse generator 45 receives an output from the square wave generator 32, and generates therefrom a short pulse in response to each transition of this square wave output. This pulse train generated by generator 45 is delayed by 80% of a half cycle to produce waveform 5 of FIG. 9, which waveform is then fed to one input of each of the AND units 42 and 43. In addition to the pulse train from delay unit 44, the AND circuit 42 receives an output from divide by two circuit 34 (waveform 2 in FIG. 9) and the AND unit 43 receives the output signal from circuit 34 after it has passed through the inverter 49.

As a result the AND circuits 42 and 43 output respectively the waveforms 6 and 7 of FIG. 9.

Thus the AND units 42 and 43 ensure that the sample and hold units 40, 41 acquire their signals in synchronism with the signals applied to their respective electrodes and at a point 80% of the way through a half cycle.

This operation is clearly shown by waveforms 8 and 9 of FIG. 9. Waveform 8 of FIG. 9 shows the rectified and amplified signal output from amplifier 36 which has been generated by the applied current pulse to the lateral electrodes 31' and illustrates the capacitive delay on the leading edge. Waveform 9 in FIG. 9 shows the output of sample and hold unit 40 with a delay of 80% of a half-cycle from the leading edge, in each case.

Comparator 46 monitors the difference between the outputs from sample and hold circuits 40 and 41 and displays the resulting value on the meter 47. As is shown in waveform 9 the result of each cycle of alternating current through a pair of electrodes produces two pulses which are input to the respective sample and hold circuit, one for each half cycle. Because of polarisation effects the amplitudes may be different but the sample and hold circuits produces an average value for the comparison in 46. Thus polarisation errors are avoided.

This arrangement is particularly advantageous since it enables the conductivity measurements in transverse and longitudinal directions to the particle orientation to be made in quick succession on a continuous flow of the fluid. Thus temperature effects are eliminated and the measurement of the aspect ratio can be made more accurately.

Although the output is shown diagrammatically as a meter output, in practice the output from comparator 46 will more commonly be used as a direct control signal for controlling admixture of particulate material or for controlling grinding apparatus to vary the particulate size. The apparatus and method are particularly appropriate for use in on-line production equipment for producing particulate solids having a desired average aspect ratio. The measuring vessels in this are formed in conduits for the particle suspension.

We claim:

1. A method of obtaining a measure of the average aspect ratio of non-spherical particles comprising the steps of:

obtaining a fully-deflocculated suspension of the particles;

causing the particles in the suspension to orientate generally in one direction;

measuring the conductivity of the particles suspension substantially in said one direction simultaneously or substantially simultaneously measuring the conductivity of the particle suspension in a direction transverse to said one direction; and using the difference in the two conductivity measurements as a measure of the average aspect ratio of the particles in suspension.

2. A method according to claim 1, wherein the particles are caused to orientate generally using a shear field by flowing the suspension through a conduit whereby the particles orientate such that their long axes are parallel to the direction of flow, which constitutes said one direction.

3. A method according to claim 1, wherein the conductivity measuring steps are alternated and repeated relatively rapidly and the results averaged.

4. A method according to claim 3, wherein each conductivity measurement is taken using an AC current.

5. A method according to claim 4, wherein the conductivity measurements are effected by using alternate full cycles of an AC square wave source for the alternate conductivity measurements.

6. Apparatus for obtaining a measure of the average aspect ratio of non-spherical particles, comprising:

a containment vessel for a fully-deflocculated suspension of the particles;

means for causing the particles in the suspension to orientate generally in one direction;

a first pair of electrodes for use in measuring the conductivity of the particle suspension in a direction aligned with said one direction;

a second pair of electrodes for use in simultaneously or substantially simultaneously measuring the conductivity of the particle suspension in a direction transverse to said one direction; and comparison means for comparing the conductivity measurements made using the first and second pairs of electrodes and for producing an output signal which is a measure of the average aspect ratio of the particles in suspension.

7. An apparatus according to claim 6, wherein one electrode is common to both pairs of electrodes.

8. An apparatus according to claim 6, wherein the electrodes are in a single containment vessel.

9. An apparatus according to claim 6, wherein at least two vessels are provided in each of which the particles in the suspension are given the same orientation, and in at least one of which the conductivity between two points in the suspension is measured in said one direction, and in at least one other of which the conductivity is measured in said transverse direction.

10. An apparatus according to claim 6, wherein the apparatus comprises a tubular containment vessel in which measurement of conductivity in the first direction is made between a first electrode which is mounted at or near the longitudinal axis of the vessel and a second, annular electrode which is mounted in the vessel surrounding and substantially coaxial with the first electrode, and in which the measurement of conductivity in the second direction is made between at least one pair of electrodes which are spaced apart longitudinally in the vessel.

11. An apparatus according to claim 6, wherein the apparatus comprises a first tubular vessel having a wall of electrically conducting material in which the measurement of conductivity in the first direction is made between an electrode mounted at or near the longitudinal axis of the vessel and the electrically conducting wall of the chamber, and a second tubular vessel in which the measurement of conductivity in the second direction is made between at least one pair of electrodes which are spaced apart longitudinally in the vessel.

12. An apparatus according to claim 10 or 11, wherein the tubular vessel or vessels form part of a conduit in a production facility, whereby the measurement of particle shape can be used in a control loop system to achieve a desired average aspect ratio by controlling admixture of particles from different sources or by control of particle grinding means.

13. An apparatus according to claim 6, wherein the electrodes are of a non-corrosive material.

14. An apparatus according to claim 13, wherein the non-corrosive material is carbon or stainless steel.

* * * * *